United States Patent [19]
Doyle

[11] Patent Number: 5,566,086
[45] Date of Patent: Oct. 15, 1996

[54] METHOD OF ENSURING ACCURATE IDENTIFICATION AND MEASUREMENT OF SOLUTES

[76] Inventor: Walter M. Doyle, 2875 Bernard Ct., Laguna Beach, Calif. 92651

[21] Appl. No.: 390,801

[22] Filed: Feb. 13, 1995

Related U.S. Application Data

[63] Continuation of Ser. No. 22,668, Mar. 1, 1993, abandoned.

[51] Int. Cl.$^6$ .................................................. G01N 21/00
[52] U.S. Cl. ........................................ 364/497; 364/498
[58] Field of Search .................................. 364/496, 497, 364/498, 499, 500; 73/1 G, 19.1, 31.03, 23.37

[56] References Cited

U.S. PATENT DOCUMENTS

| | | | |
|---|---|---|---|
| 3,150,516 | 9/1964 | Linnenbom et al. | 73/19.1 |
| 4,449,820 | 5/1984 | Koizumi et al. | 356/315 X |
| 4,496,839 | 1/1985 | Bernstein et al. | 250/341 |
| 5,043,286 | 8/1991 | Khalil et al. | 436/136 |
| 5,046,846 | 9/1991 | Ray et al. | 364/498 X |
| 5,080,485 | 1/1992 | Sperling | 356/315 |
| 5,083,283 | 1/1992 | Imai et al. | 364/497 |
| 5,121,337 | 6/1992 | Brown | 364/498 |
| 5,127,259 | 7/1992 | Kahl et al. | 73/19.1 |
| 5,242,602 | 9/1993 | Richardson et al. | 364/498 X |
| 5,262,961 | 11/1993 | Farone | 364/500 |
| 5,315,528 | 5/1994 | L'vov | 364/498 |

OTHER PUBLICATIONS

Doyle et al. "Fourier Transform–Infrared Chemical Reaction Monitoring Using an In situ Deep Immersion Probe" Spectroscopy, Jan. 1990, vol. 5 No. 1 pp. 34–38.
American Laboratory, Dec. 1991, McIntosh et al., "Real-time Waste Stream Monitoring", pp. 19–22, see pp. 19–22.
8th International Conference on Fourier Transform Spectroscopy, 1–6, Sep. 1991, Doyle, W. M., "Analysis of Trace Concentrations of Contaminants in Water by Sparging–FTIR" pp. 199–200, see pp. 199–200.
Pollution Prevention in Industrial Processes, 1992, Fleming et al., "On–Line Analyzer for Chlorocarbons in Wastewater", Chapter 6, see pp. 48–61.

*Primary Examiner*—Emanuel T. Voeltz
*Assistant Examiner*—M. Kemper
*Attorney, Agent, or Firm*—Plante & Strauss

[57] ABSTRACT

A method is for expanding the solute-identifying capabilities of an infrared (IR) sparging system. In IR-sparging, bubbles transfer solutes contained in a volume of liquid to a gas stream which is analyzed in a gas cell. FTIR spectrometry provides spectral absorbance analysis to identify and measure the solutes. By repeating the spectral scans at given time intervals, data is also obtained which is related to the depletion rate curves of the respective solutes. Using this depletion rate data to complement the spectral analysis data provides major benefits in successfully identifying the solutes.

20 Claims, 9 Drawing Sheets

METHOD OF ENSURING ACCURATE IDENTIFICATION AND MEASUREMENT OF SOLUTES

This application is a continuation of application Ser. No. 08/022,668, filed Mar. 1, 1993 now abandoned.

BACKGROUND OF THE INVENTION

This invention relates to the use of spectral absorbance data, as obtained for example by FTIR spectroscopy, to identify and/or measure the concentration of solutes in a volume of liquid. A common purpose is to identify and measure pollutants in waste water discharge.

In common assignee U.S. Pat. No. 5,218,856, concentration of any given solute in a body of liquid is accurately determined by using an FTIR gas cell to measure the solute depletion as a function of time, making use of the exponential decay of the solute which occurs as a fixed volume of liquid is sparged at a constant air flow rate. This provides an accurate measurement of solute concentration in the body of liquid. The term "sparging" refers to a process of causing an air bubble stream to flow through a volume of water. Solutes in the water combine with the air bubbles, and travel to a gas cell, in which they are subjected to spectral absorption analysis. An IR gas cell in an FTIR spectrometer is preferred as the analytical instrument.

The ease or difficulty of analysis by IR-sparging depends in part on the number of solutes in the water, and on the prior knowledge of their identities. The use of FTIR for multi-component analysis is limited by the fact that it monitors all components simultaneously. This fact is both a strength and a weakness. On the one hand, it makes it possible to perform a much faster analysis than with a separation technique, such as gas chromatography (GC). But, on the other hand, it makes it difficult, if not impossible, to monitor large numbers of components in a given volume of liquid. Because of the fact that the measured spectrum will be the combination of the spectra of all components present, it is necessary to know in advance the identities of the components that may occur, and to set up a calibration for these components. In contrast, GC separates the various components based on the passage of time. While GC doesn't always positively identify an unknown component, it can determine how many components are present, and can get a good idea of their nature. FTIR is often combined with GC to positively identify the components (GC fractions) once they have been separated. In summary, GCIR can provide the desired data, but it causes a significant loss of time, which the present application seeks to change.

The present invention involves a discovery which permits the individual identification of multiple solutes in a sparging-IR system, without necessitating component separation by the use of chromatography.

SUMMARY OF THE INVENTION

The present invention uses the time expiration concentration decay curves that occur when gas is sparged through a volume of liquid containing one or more dissolved substances to provide information regarding the identities and/or concentrations of the solutes. In the preferred embodiment, the time dependent information is combined with spectral information, such as that obtained by means of an IR spectrometer, to provide a two dimensional set of data for analysis purposes.

The solute vapor stream obtained from the sparging vessel is directed to a gas cell attached to an infrared spectrometer. Successive spectra, consisting of discrete sets of absorbance values as a function of infrared frequency, are recorded at a chosen time interval, such as every ten seconds. The absorbance at a given frequency may include contributions from more than one solute. Usually, for a constant gas flow rate, the concentration of a given solute will follow an exponential depletion curve as a function of time. In this case, the dependence of absorbance on time at a given frequency will be a sum of the exponential curves corresponding to the various solutes which absorb at that frequency. By fitting the measured time dependent curve to a sum of exponentials, a measure is obtained of the contribution of each solute to the absorbance at the specified frequency. By making use of this type of information for all relevant frequencies, the ability to analyze liquids containing multiple solutes is greatly enhanced.

If the contributions at each spectral frequency having exponential decay rates within some predetermined range are identified, the time zero absorbance values of these contributions can be used to construct a composite spectrum corresponding to the substances present with decay rates within this range. This spectrum can be used in conjunction with known (or ascertainable) spectral and decay rate information for solutes which might be present, and with any one of the available multivariate quantitative analysis programs to determine the concentrations of the substances present.

In effect, the present invention uses time dependent spectral information (obtained while solutes are being depleted) to construct a two dimensional matrix of data which can be used to expand the ability to use multivariate analysis to monitor concentrations of solutes.

DETAILED DESCRIPTION OF SPECIFIC EMBODIMENTS

Using spectral information provided by an analytical instrument, such as an FTIR spectrometer, a multicomponent concentration analysis can be carried out by one of several different mathematical techniques. The feasibility of a specific technique is influenced by such factors as the number of solutes in the volume of liquid, and the presence or absence of knowledge as to what substances are included among the solutes.

The relatively straightforward "P" matrix approach is adequate for most situations. A "P" matrix calibration is equivalent to setting up a series of simultaneous equations relating the radiation absorbances at a finite set of frequencies to the concentrations of the substances that may be present. In doing this, one tries to select a set of absorbance radiation frequency channels which make the greatest possible distinction between the various chemical species. The equations are of the form:

$$A_1 = K_{1,1}C_1 + K_{1,2}C_2 + K_{1,3}C_3 + \text{etc};$$

$$A_2 = K_{2,1}C_1 + K_{2,2}C_2 + K_{2,3}C_3 + \text{etc};$$

$A_1$ is the total absorbance in channel 1, $C_1$ is the concentration of the species 1, and $K_{1,1}$ is the experimentally determined coefficient giving the contribution of species 1 to absorbance 1.

The set of equations can be written in the matrix form, $$A = KC$$

where K represents the two-dimensional array (matrix) of coefficients of the form, $K_{x,y}$.

Once the calibration has been performed by using a set of known samples to determine the values of the "K" matrix elements (coefficients), the set of equations can be solved to express the concentrations in terms of the absorbances. In matrix form, the solution is:

$$C = PA$$

where the "P" matrix is the inverse of the "K" matrix. Given a measured spectrum resulting from the presence of a mixture of the possible substances, one merely has to perform a matrix multiplication by the "P" matrix to determine the concentrations of the various substances.

The "P" matrix approach becomes progressively more difficult to apply as the number of possible solutes increases, with something like 15 typically considered a maximum for a reliable analysis. In addition, the approach breaks down if the sample includes a solute that was not anticipated in the calibration.

The present patent application concerns a method for alleviating this problem. In brief, the method disclosed in this application makes use of the exponential decay characteristics of a given analysis to help identify the substances present, and to measure their concentrations. This information can be used in a variety of ways.

The common assignee U.S. Pat. No. 5,218,856, referred to above, discloses a novel method of determining the initial concentration of any given solute in a volume of liquid. The process used is referred to as "IR-sparging". It uses a series of time-spaced FTIR spectra to create a depletion curve for each solute.

Because each solute has a unique exponential depletion curve, the depletion curve provides new, additional solute identification information, which is invaluable as a complement to the spectral information provided by FTIR analysis. As will be discussed below, there are some substances, such as carbon dioxide ($CO_2$) whose depletion curves are not truly exponential, thereby creating some complications in the solute identification process.

Before detailed explanation of the present invention is undertaken, it will be useful to discuss briefly certain material from U.S. Pat. No. 5,218,856, FIGS. 1–3 of this application are substantially identical to FIGS. 1–3 of that application.

Figure 1:
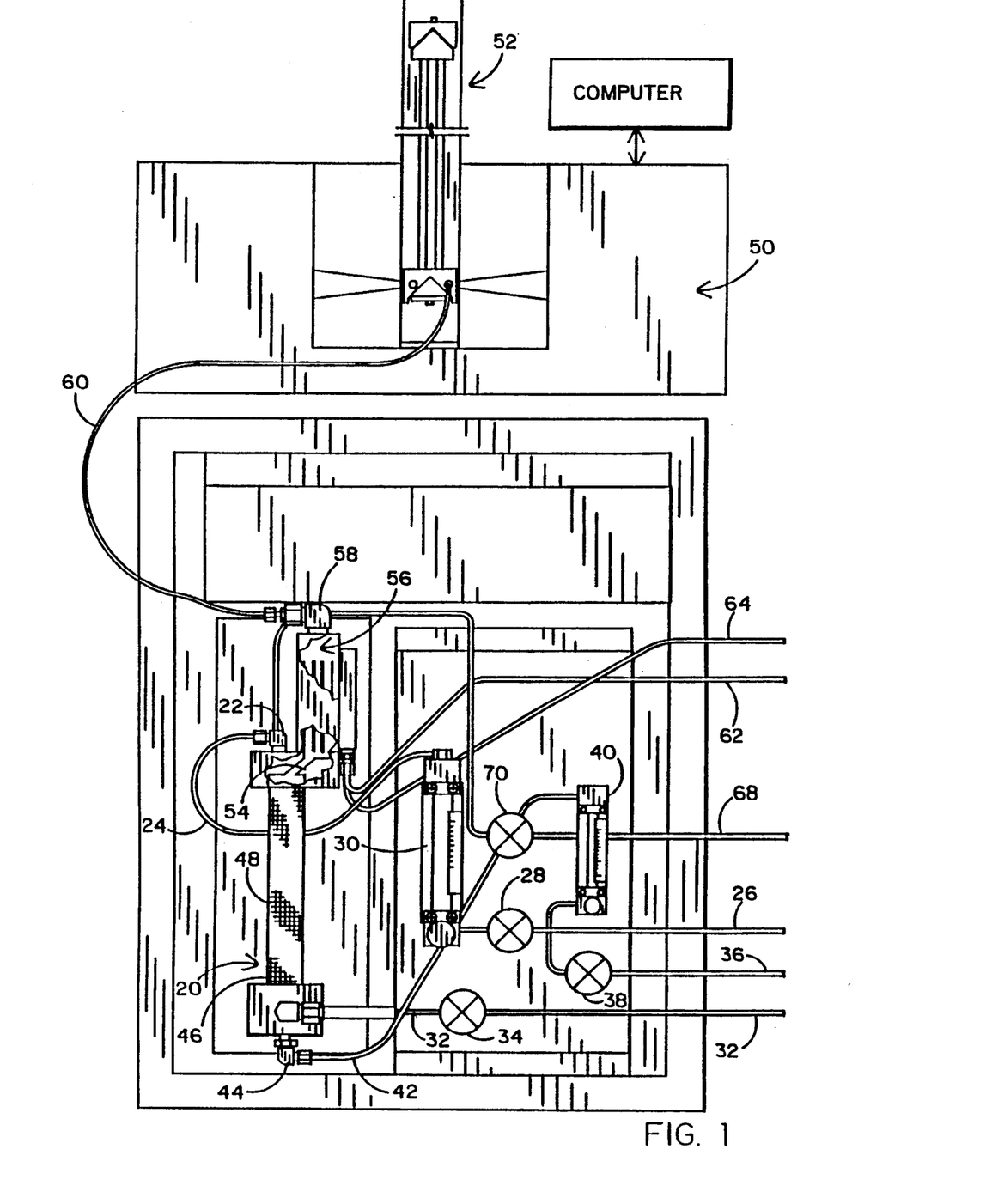
FIG. 1, which corresponds to FIG. 1 in common assignee U.S. Pat. No. 5,218,856, is a schematic showing components which can be used in an IR-sparging apparatus, for the purpose of generating both spectral absorption and concentration decay curves for solutes in a volume of liquid.

FIG. 1 shows diagrammatically (in a vertical plane) an apparatus which can be used to perform IR-sparging. Other combinations of components could be used, if desired. A sparging vessel 20 contains the liquid (usually water) whose solutes are to be identified and measured. Liquid enters vessel 20 through a fitting 22 at the top of the vessel, from an input pipe 24. Starting at the right side of the figure, a water input pipe 26 leads to a flow control valve 28, after which the water passes through a velocity gauge 30, on its way to pipe 24. When water exits the sparging vessel 20, it flows through a drain pipe 32, passing through a flow control valve 34.

The air (or other gas), which creates the sparging effect by causing bubbles to rise inside the sparging vessel, enters through a pipe 36 (right side of drawing), passes through a flow control valve 38, a velocity gauge 40, and then pipe 42; and enters the bottom of the sparging vessel via a fitting 44.

The sparging bubbles are emitted into the water in the vessel 20 by a short, vertically-extending nozzle 46, which has a very large number of tiny holes for emitting air. The air moving through these holes forms bubbles, shown at 48, which rise through the water in the vessel. The bubbles combine with vaporized contaminants in the water to provide a suitable gas for analysis in a gas cell, which is part of an infrared spectrometer.

The infrared spectrometer is shown generally at 50. The gas cell, shown at 52, may incorporate, for example, the structural concepts described in common assignee U.S. Pat. No. 5,065,025. By means of interferometric analysis of the gas flowing in gas cell 52, the constituents in the gas are identified and measured. The bubbles in the waste water provide a large air-liquid surface area for passage of dissolved volatile material (contaminants) into the gas phase of the analytical system.

The gas which carries the contaminants leaves the sparging vessel via a short pipe 54, which connects to the bottom of a condenser 56. Gas passes from the top of condenser 56 at a fitting 58, and flows to the gas cell 52 via a pipe 60. The desired temperature in condenser 56 is maintained by controlling the flow of cooling water in inlet and outlet pipes 62 and 64.

The solute depletion rate is determined using a static body of water in the vessel. Gas is sparged through a non-flowing volume of water for the purpose of determining both the initial concentration and the depletion rate for each contaminant.

Figure 2:
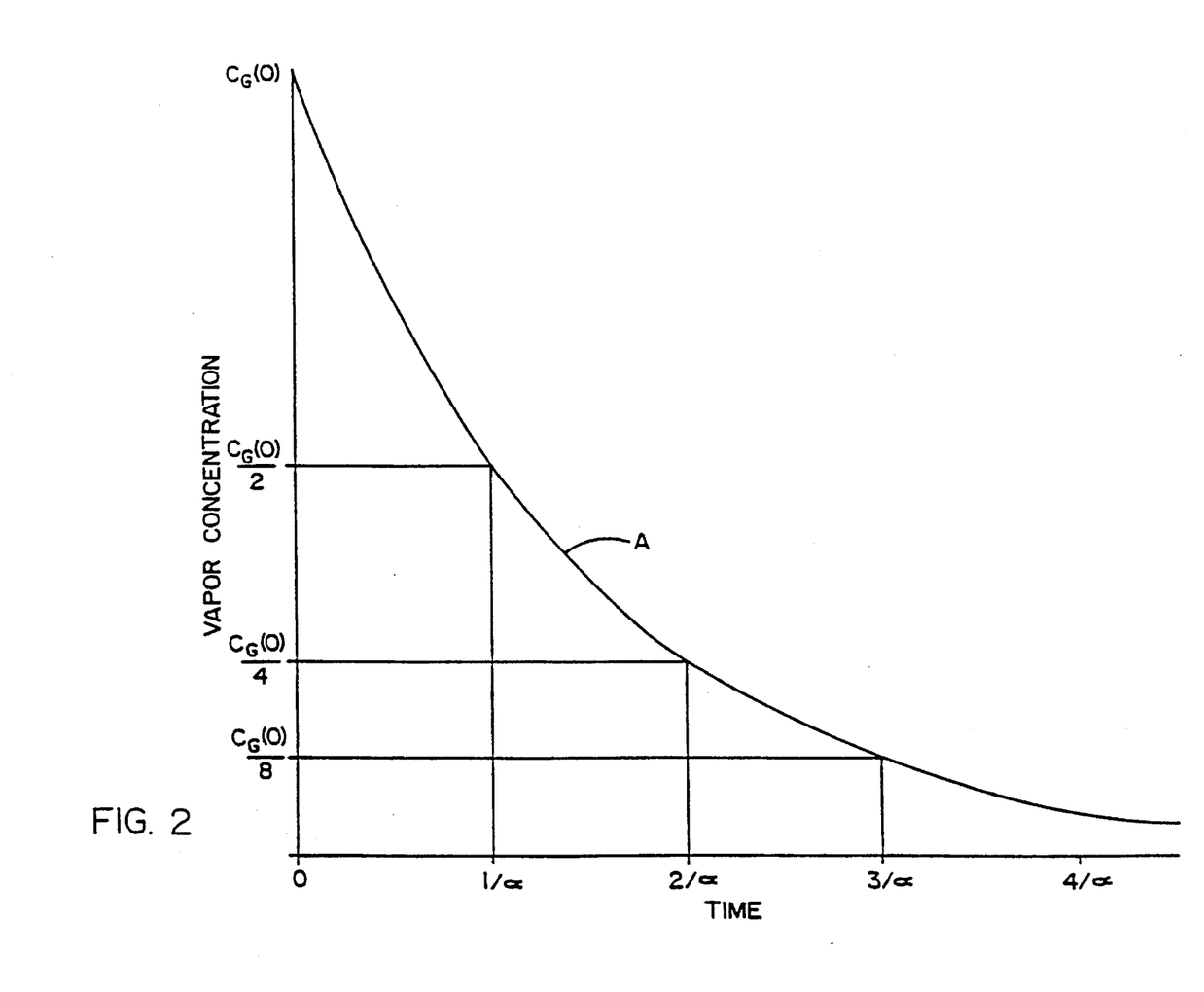
FIG. 2, which corresponds to FIG. 2 in U.S. Pat. No. 5,218,856, is a graph showing a curve which plots vapor concentration of a given solute against elapsed time.
Figure 3:
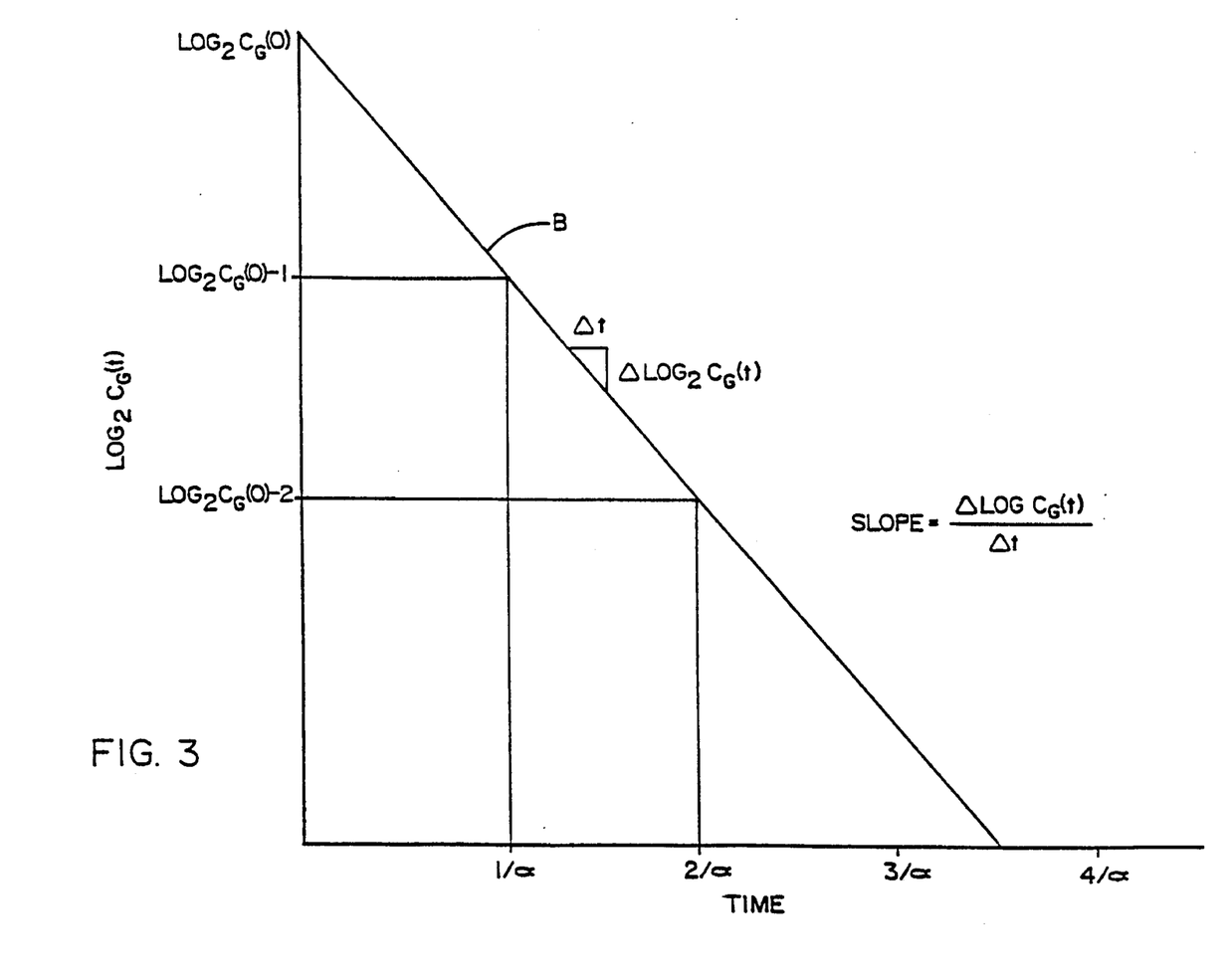
FIG. 3, which corresponds to FIG. 3 of U.S. Pat. No. 5,218,856, is a graph based on FIG. 2, in which the data has been converted to logarithm values.

FIGS. 2 and 3 illustrate the unique depletion curve of a specific solute. In both figures, time-related values are distributed along the X-axis, and vapor concentration-related values are distributed along the Y-axis. FIG. 2 has a curve, A, illustrating the change in concentration as time elapses during sparging. The X-axis values are $1/\alpha$, $2/\alpha$, $3/\alpha$ and $4/\alpha$, in which $\alpha$ (alpha) represents a depletion rate constant. The reciprocal of $\alpha$ is the depletion half life. At the top of the Y-axis, the curve represents the concentration of the substance before any depletion has occurred, i.e., at time zero. When the elapsed time reaches the value represented by 1/α, the concentration will have dropped to one-half of its initial (time zero) value. At time 2/α, the concentration will be one-fourth of its initial value; and at time 3/α, the concentration will be one-eighth of its initial value.

FIG. 3 has a straight-line slope B in which the concentration data of FIG. 2 is presented as the logarithmic equivalent, thus converting the curve A into a straight-line slope B. The logarithmic values simplify the determination of the vapor concentration value at time zero, $C_G(0)$.

The starting concentration, before the onset of depletion, has been determined by measuring the concentration at any two later times and then extrapolating back to time zero. This fact can be quite useful for the open loop measurement of solutes having low solubilities and hence fast depletion times. This measurement of solute concentration was a primary benefit disclosed in U.S. Pat. No. 5,218,856, which relied on the unique depletion curve of each solute.

The present invention, as stated above, uses the unique time expiration decay curve of each solute substance to provide a second dimension for solute identification purposes. The first dimension is the usual spectrographic absorbance data in which a spectrograph plots infrared frequency (or the reciprocal wave numbers) on the X-axis, and plots spectral absorbance values on the Y-axis. The infrared spectrometer which analyzes the contents of the gas cell in the IR-sparging apparatus of FIG. 1 provides infrared frequency spectral absorbance scans at whatever time spacing has been selected, e.g., every ten seconds. The time between successive scans provides depletion data for each point or channel in the spectral range. Thus, the spectral absorbance data and the time depletion data are both collected by operation of the IR-sparging apparatus shown in FIG. 1.

The use of depletion rate information to complement the basic spectral absorbance information in the analysis of solutes (usually impurities) in a volume of liquid can be valuable in at least the following four situations:

I. To confirm that one of more substances detected in a liquid stream are indeed the substances included in the calibration.

II. To expand the number of components contained in the calibration set of an analysis, by taking into account their depletion rates.

III. To generalize the analysis so as to handle a large number of components by grouping them into sets having depletion rates which fall within specified ranges.

IV. To identify unanticipated substances.

Each of these four situations will now be discussed in detail.

Figure 4:
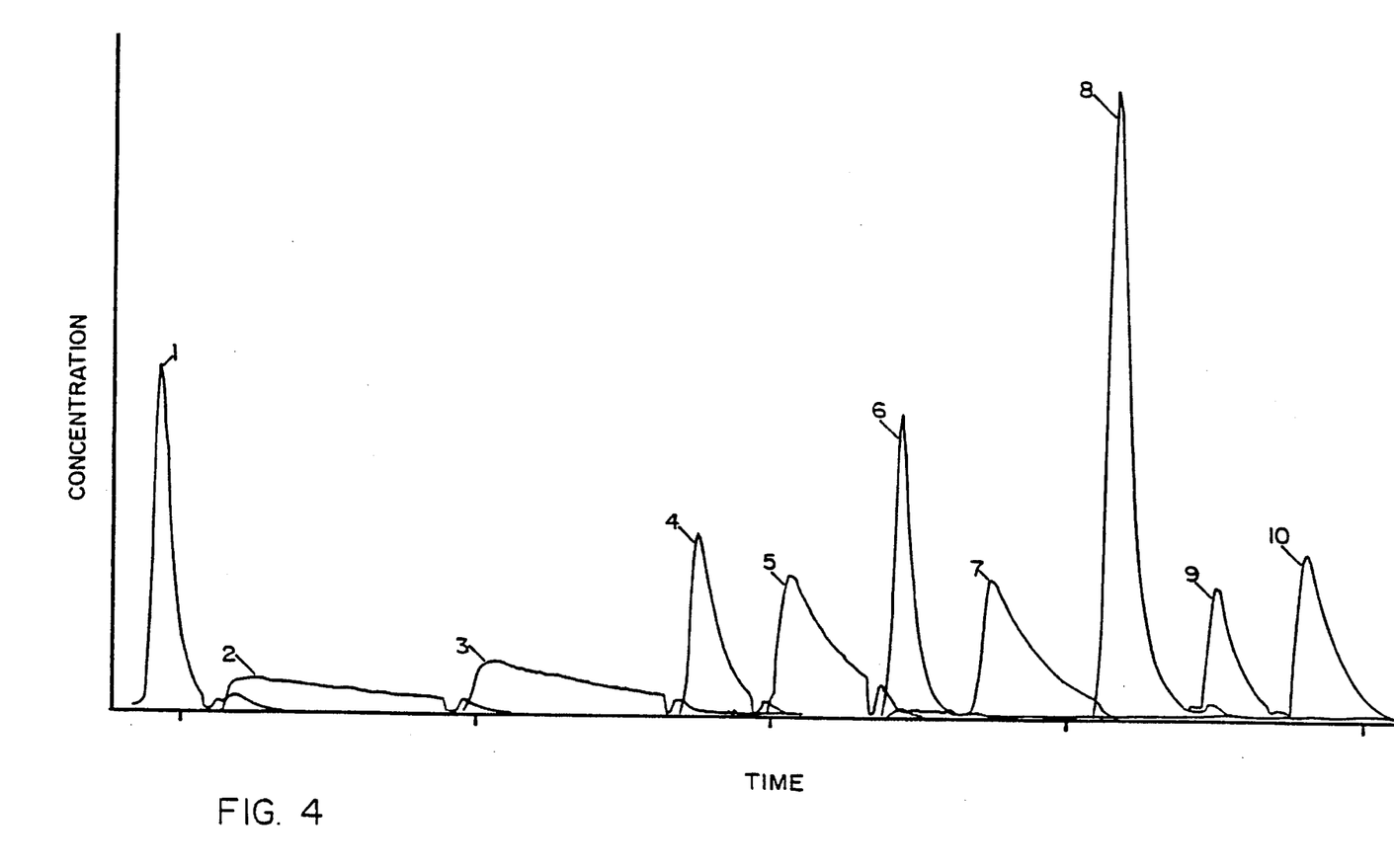
FIG. 4 is a graph showing depletion curves for 10 different solutes, measured one after the other, plotting concentration on the Y axis against time on the X axis.

I. The use of depletion rate information to confirm that one or more detected substances are the substances included in the calibration. FIG. 4 shows the depletion curves for ten different solutes measured with a constant air flow rate and a calibration matrix set up for these solutes.

The ten substances are: (1) 111-trichloroethane, (2) 112-trichloroethane, (3) 12-dichloroethane, (4) trn-dichloroethane, (5) cis-dichloroethane, (6) carbon tetrachloride, (7) chloroform, (8) perchloroethylene, (9) trichloroethylene, and (10) dichloroethylene. As can be seen, the various substances exhibit a very wide range of depletion rates. Each substance has its own unique depletion rate constant—subject, of course, to dependence on gas flow rate, temperature and other factors, discussed in U.S. Pat. No. 5,128,856. In most situations, if the temperature of the water is known, it will be possible to predict fairly accurately what-depletion rate to expect for a given substance.

Assume that a substance appears in the wastewater stream that was not anticipated in doing the calibration. This substance may have spectral characteristics which give rise to concentration readouts corresponding to one or more of the substances included in the calibration. Indeed, in a continuous flow sparging-IR analysis, it would be concluded that the substances present corresponded to those predicted by concentration readouts. However, with static sample depletion analysis, the measured depletion rates can be compared with the known values for the calibration samples. If the depletion rates are not correct, it is clear that a new substance is present. At this point, one might try to determine what the new substance is by examining the spectrum, or performing a GC or GC-IR run. Once this has been done, a new calibration can be set up taking into consideration the new substance.

Figure 5:
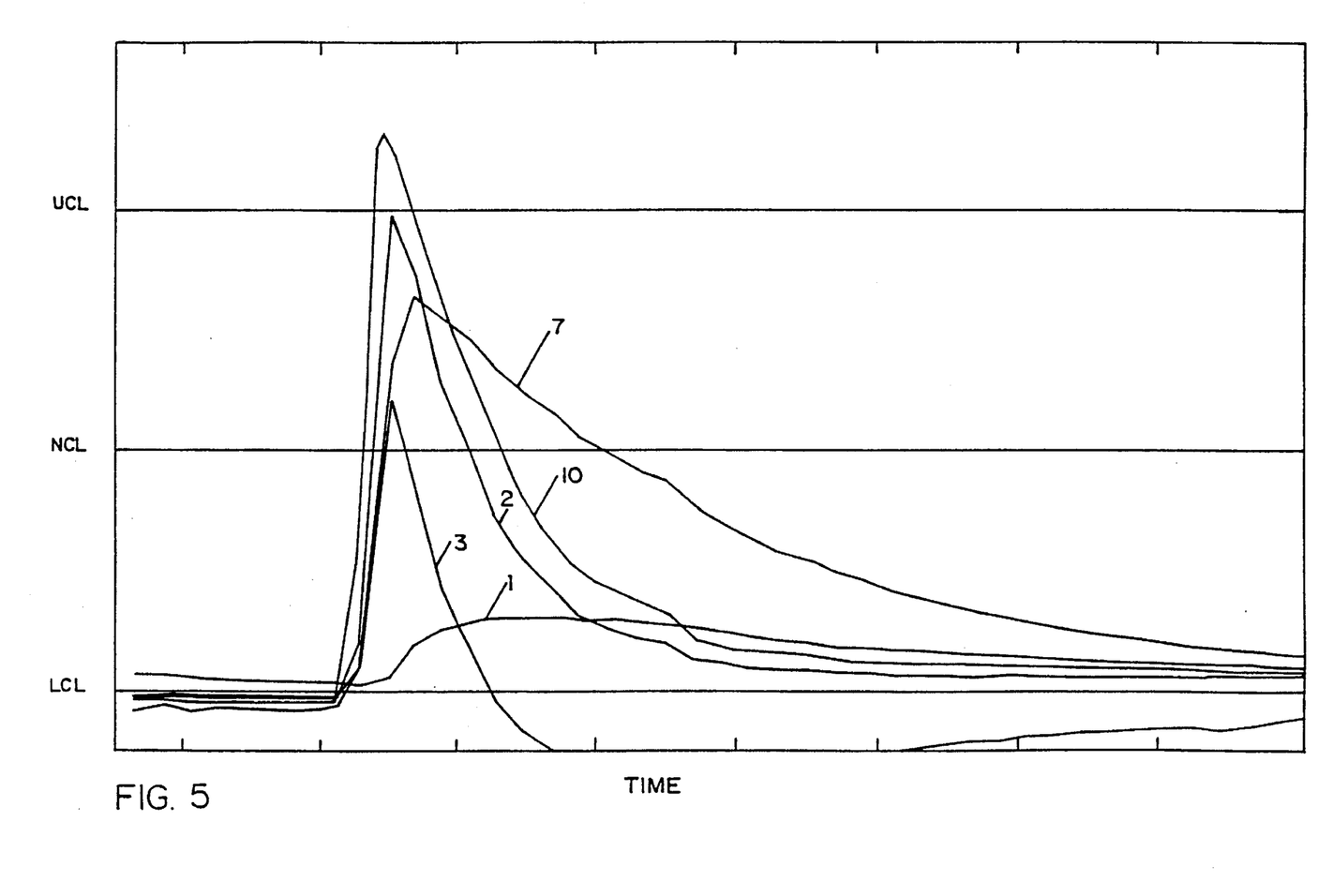
FIG. 5 is a graph based on an analysis, accomplished by a sparging system, of an unknown water sample, with the analyzer calibrated for certain listed substances.

FIG. 5 is an example of some data corresponding to an unknown sample run with the same calibration matrix as FIG. 4. In this case, the presence of chloroform was expected, but it was not known what else might be in the sample. Positive readings were obtained for concentration channels 1, 2, 3, 7, and 10.

Figure 6:
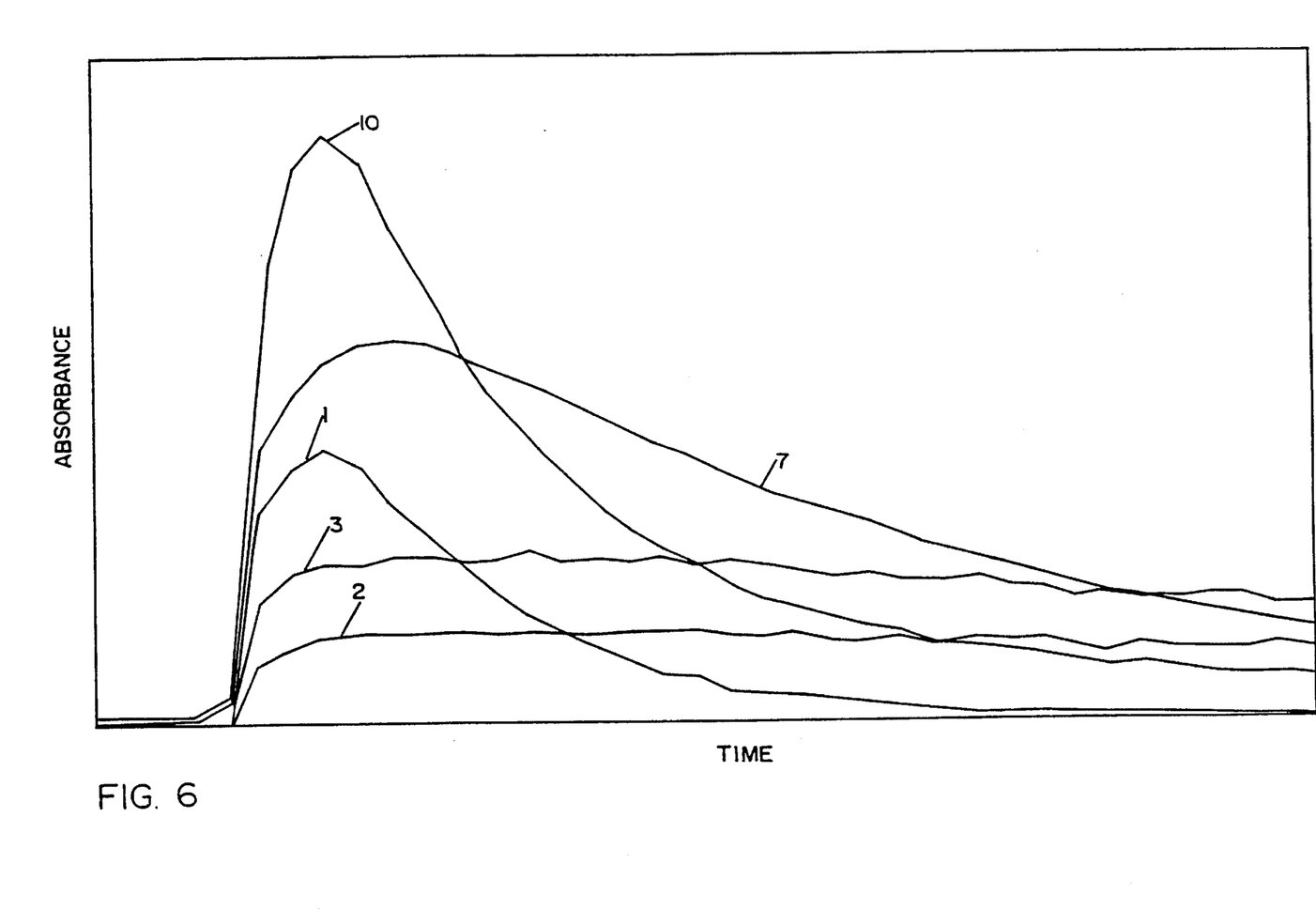
FIG. 6 is a graph based on an analysis, accomplished by a sparging system, of a water sample containing the five solutes corresponding to the analysis channels for which FIG. 5 showed responses.

FIG. 6 gives the concentration plots for the same concentration channels as those in FIG. 5, after simultaneous injection of the solutes used to obtain the calibration matrix. After compensating for the difference in flow rate, channel 7 (chloroform) can be seen to have the expected depletion rate. However, the depletion rates for the other four channels (1, 2, 3, and 10 as seen in FIG. 5) were completely different from the calibration solutes.

II. The use of depletion rate information to expand the number of components contained in the calibration set of an analysis. This approach is appropriate for use with "P" matrix calculations or other methods in which discrete IR-bands are chosen as the input data. It improves on the conventional matrix approach by using depletion rate information to effectively reduce the amount of overlap (or interference) between species which absorb in the same spectral region. A typical procedure would be as follows:

1. Obtain spectra and depletion rate information for each of the pure substances to be included in the calibration.

2. Set up a "P" matrix calibration in the conventional way, starting by identifying and selecting those bands which do not involve overlaps, i.e., each of which is characteristic of only one substance.

3. From the spectral regions which exhibit overlap, select spectral channels within which only two of the species overlap and for which these species have the greatest difference in depletion rate. In setting up the matrix, each of these channels will be treated as if it consisted of two separate channels, one for each species. The interference is simply ignored.

4. If necessary, apply the same procedure to spectral regions in which three species overlap, and continue the procedure until enough channels have been selected to complete the matrix. In some cases, the rate constants may not be sufficiently distinct to allow reliable separation of the substances. In matrix terminology, these cases would represent the nondiagonal or cross-terms in the matrix. The matrix calculation can handle such terms as long as they are not too numerous or severe.

5. When analyzing a wastewater sample, record IR absorbance as a function of time for each of the channels chosen in steps 2, 3, and 4.

6. For each channel that does not involve overlap, fit the known exponential depletion curve of the corresponding species to the decay curve, using any of the mathematical curve fitting routines available for this purpose. This will result in the determination of an amplitude coefficient equal to the absorbance at time zero. This can be used to calculate the concentration at t=0.

7. For each channel that involves overlap, fit the depletion curve to the previously measured exponentials for the species known to absorb in this region. The amplitude coefficients obtained will be used as the absorbance values for respective species.

8. Perform the "P" matrix multiplication to obtain the concentrations of the various species.

III. The use of depletion rate information to generalize an analysis by grouping components into sets having depletion rates which fall within specified ranges. The previous example can be thought of as an enhancement of the matrix approach to quantitation. This example outlines a more generalized approach that can be applied in conjunction with almost any method of multiple component analysis.

1. Identify all organic compounds which might occur in a given stream and divide them up into groups falling within specified ranges of depletion rate constants. The number of different ranges selected will depend partly on the total number of substances to be included and the required sensitivity. The number of substances within any one group should be kept to approximately 15 or less.

Identify a desirable set of absorbance channels for use in distinguishing the various components. One scheme would be to first divide the fingerprint region of the spectrum (e.g., 400 to 1800 $cm^{-1}$) into a series of adjacent channels with widths of perhaps 8 or 16 $cm^{-1}$. To this, add channels corresponding to common higher frequency functional groups of chemical interest, such as the C-H stretch, CNO mode, etc.

3. Perform a multivariate calibration for all of the substances in each rate constant group using an appropriate set of samples and any of the available computerized methods. The spectral channels chosen in step 2 should be used as the spectral basis for this calibration.

4. Record a background (or reference) spectrum immediately before starting to acquire data for a wastewater sample to be analyzed to obviate the need to record localized baseline points.

5. While performing open loop, static sample sparging, record the absorbance as a function of time for each of the predetermined channels of step 2. In doing this, all of the data points within each channel can be averaged to improve sensitivity.

6. For each absorbance channel, perform a mathematical fit of the depletion curve to a sum of exponential decay functions, varying the amplitude and decay constant of each exponential function to obtain the best fit. Various mathematical methods, such as PLS (partial least squares), are available for performing this calculation.

This exercise should lead to a finite number of different rate constants, with the exponentials having the same decay constant occurring in more than one channel. For each distinct rate constant, the set of amplitudes calculated in this step 6 for the various channels constitutes a composite spectrum for substances present with that rate constant.

7. Add together all of the composite spectra for rate constants falling in each of the groups chosen in step 1. This obviates the need to determine whether nearly identical rate constants obtained for two different spectral channels correspond to the same or to different species.

8. Calculate the concentration of the species present by applying the chosen multivariate technique and the calibrations developed in step 3 to each of the depletion rate groups established in step 1.

IV. The use of depletion rate information to identify unanticipated substances without prior multivariate calibration. This approach is analogous to the use of GC-IR to separate and identify unknown substances. However, in this case, the depletion rate data provides the equivalent of a low resolution chromatograph.

1. Identify a desirable set of absorbance channels for use in distinguishing the various components. One scheme would be to first divide the fingerprint region of the spectrum (e.g., 400 to 1800 $cm^-$) into a series of adjacent channels with widths of perhaps 8 or 16 $cm^-$. To this, add channels corresponding to common higher frequency functional groups of chemical interest, such as the C-H stretch, CNO mode, etc.

2. Record a background (or reference) spectrum immediately before starting to acquire data for a wastewater sample to be analyzed to obviate the need to record localized baseline points.

3. While performing open loop, static sample sparging, record the absorbance as a function of time for each of the predetermined channels of step 2. In doing this, all of the data points within each channel can be averaged to improve sensitivity.

4. For each absorbance channel, perform a mathematical fit of the depletion curve to a sum of exponential decay functions, varying the amplitude and decay constant of each exponential function to obtain the best fit. Various mathematical methods, such as PLS (partial least squares), are available for performing this calculation.

This exercise should lead to a finite number of different rate constants, with the exponentials having the same decay constant occurring in more than one channel. For each distinct rate constant, the set of amplitudes calculated in this step 6 for the various channels constitutes a composite spectrum for substances present with that rate constant.

5. Examine the spectra corresponding to each distance rate constant identified in step 4. For some, if not all, of the rate constants, it may be possible to determine that a single component is present and to identify this by searching the spectrum against a library of gas phase spectra. Even if the library search does not identify a good fit, an analysis of the functional groups present can provide an indication of the general nature of the substance or substances being analyzed.

In the case of an accidental spill, it is likely that only one, or perhaps a few, species will be present. In this case, this approach IV should be entirely adequate. It has the advantage of allowing the identification of substances which may not have been included in a calibration set.

The foregoing examples illustrate the analytical power of combining depletion rate information, obtained by IR-sparging, with the basic FTIR spectral absorbance techniques.

There are two further problems which should be considered. Both relate to possible sources of confusion. One relates to the sums of decay rates which may be observed, representing a plurality of substances. The other relates to the existence of substances whose decay rates are not purely exponential, such as carbon dioxide ($CO_2$).

In applying this method, it is often necessary to fit a sum of exponential functions to an experimentally measured depletion curve. To explain this, assume that the depletion function, i.e., measured absorbance as a function of time, is a pure exponential for each substance present. This will generally be true as long as the sample temperature is constant and the various substances being sparged out of the water sample are present in reasonably low concentrations. The assumption may not be true if one or more of the substances is present at high concentration. In this case, the solubility of the remaining substances may change as the high concentration substance is removed. This will give rise to a change in the partitioning function and hence a departure from the assumed exponential depletion function. Nevertheless, the exponential assumption will be reasonably valid for most applications.

Figure 7:
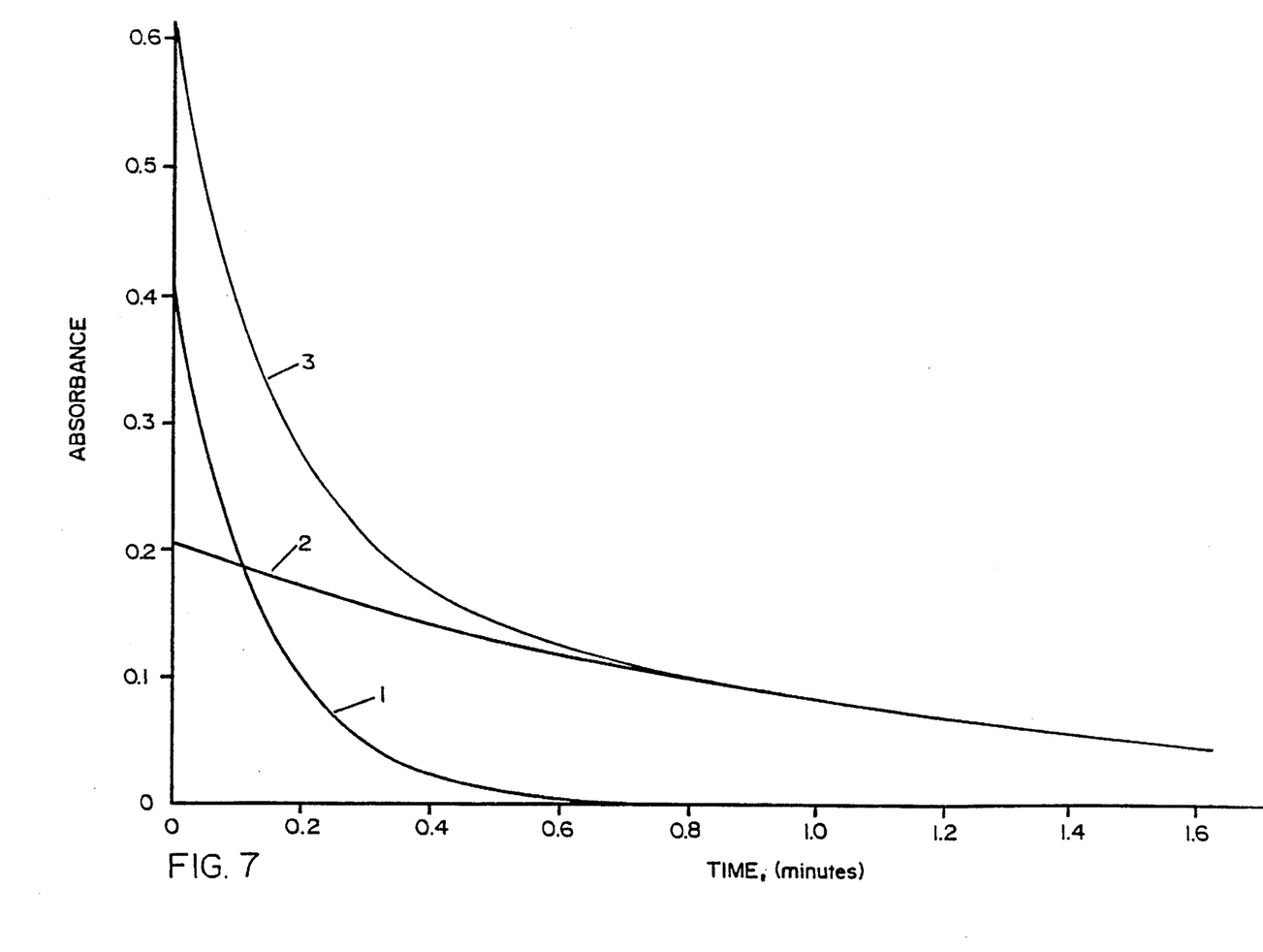
FIG. 7 is a graph showing 3 curves, which illustrate the effect of adding together two different exponential depletion curves.

To understand what is involved in fitting a measured depletion curve to a sum of exponentials, consider FIG. 7. Here, curves 1 and 2 are pure exponentials, having the functionality $$A_n = A_n(O) e^{-\alpha_n t}$$

where "n" can be either 1 or 2. Curve 3 is the sum of curves 1 and 2.

As the equation indicates, an exponential function is uniquely specified by two parameters: its value $A_n(O)$ at time=0 and its depletion rate constant, $\alpha_n$. The values of these parameters for curves 1 and 2 are:

| $A_1(O) = 0.4$ | $\alpha_1 = 10$ |
|---|---|
| $A_2(O) = 0.2$ | $\alpha_2 = 1.25$ |

If curve 3 represented the measured depletion curve in a given spectral region, then curves 1 and 2 would represent the contributions in this spectral region due to the two substances having depletion rate constants of 10 and 1.25, respectively.

It should be noted that curve 3 is not a pure exponential function but is the sum of two specific exponentials. No other combination of exponentials would give rise to this same curve. The combination of functions required to fit a given measured depletion curve can be determined by any of a number of different mathematical curve fitting methods. One of the most common of these is the "least squares" method (see Mathematics of Physics and Modern Engineering, pg. 702).

Curve fitting is a trial and error technique. Before the advent of digital computers, it was often done graphically and laboriously. Today, it can be done rather rapidly, using modern computers. In the present case, the process is aided by the fact that the curve is known to be a sum of exponentials, all having their starting points at the same time. The computer merely has to try various combinations of initial values and depletion rate constants until it finds the best fit. This occurs when the square of the sum of the deviations between the points on the measured curve and the fitted curve reaches a minimum value.

The degree of difficulty in performing the curve fitting routine will depend on the extent to which it is known what to look for. The easiest case would be a situation such as Example II above, in which it is known what species can contribute in a given spectral region and what their depletion rates should be. Thus, a reasonable assumption can be made about the various $\alpha_n$ values. All that is necessary is to vary the values of $A_n(O)$ to find the best fit. In some cases, it may also be desirable to vary the $\alpha_n$ values around the assumed starting values to account for variations in the physical condition of the water sample (e.g., temperature).

The methods described in Examples III and IV above would require a more generalized least squares curve fitting routine, in which all the $\alpha_n$ and $A_n(O)$ values are varied. For a given spectral region more different exponentials can be progressively added until a good fit is obtained. The number of exponentials required will be an indication of the number of chemical components contributing to this spectral region. As additional spectral regions are investigated, it would be a good idea to first try using the rate constants already identified. Since a given chemical species is likely to contribute to multiple spectral regions, this should accelerate the fitting process.

Figure 8:
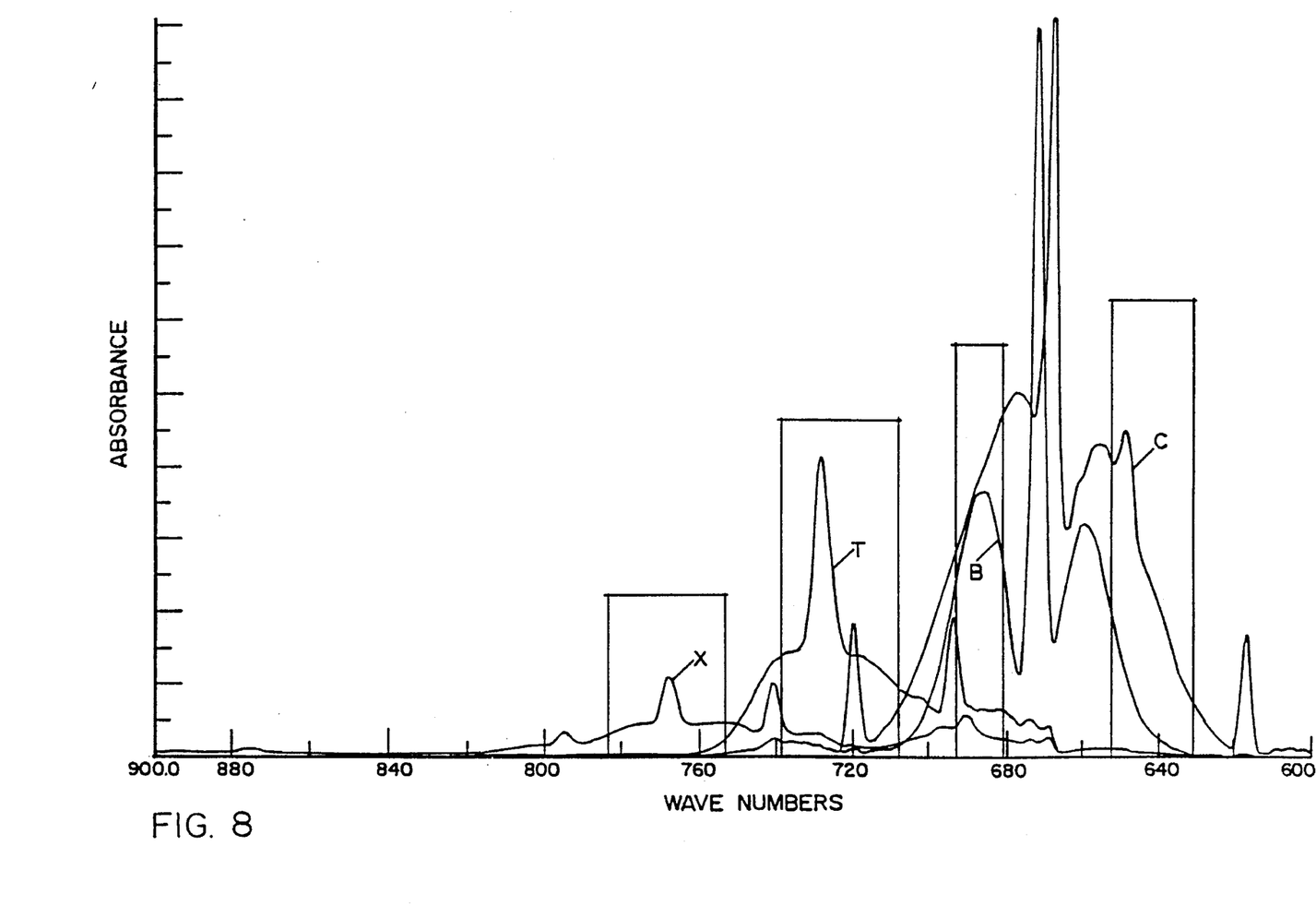
FIG. 8 is a graph in which the fingerprint region spectra of four specific substances have been superimposed to illustrate their overlap.
Figure 9:
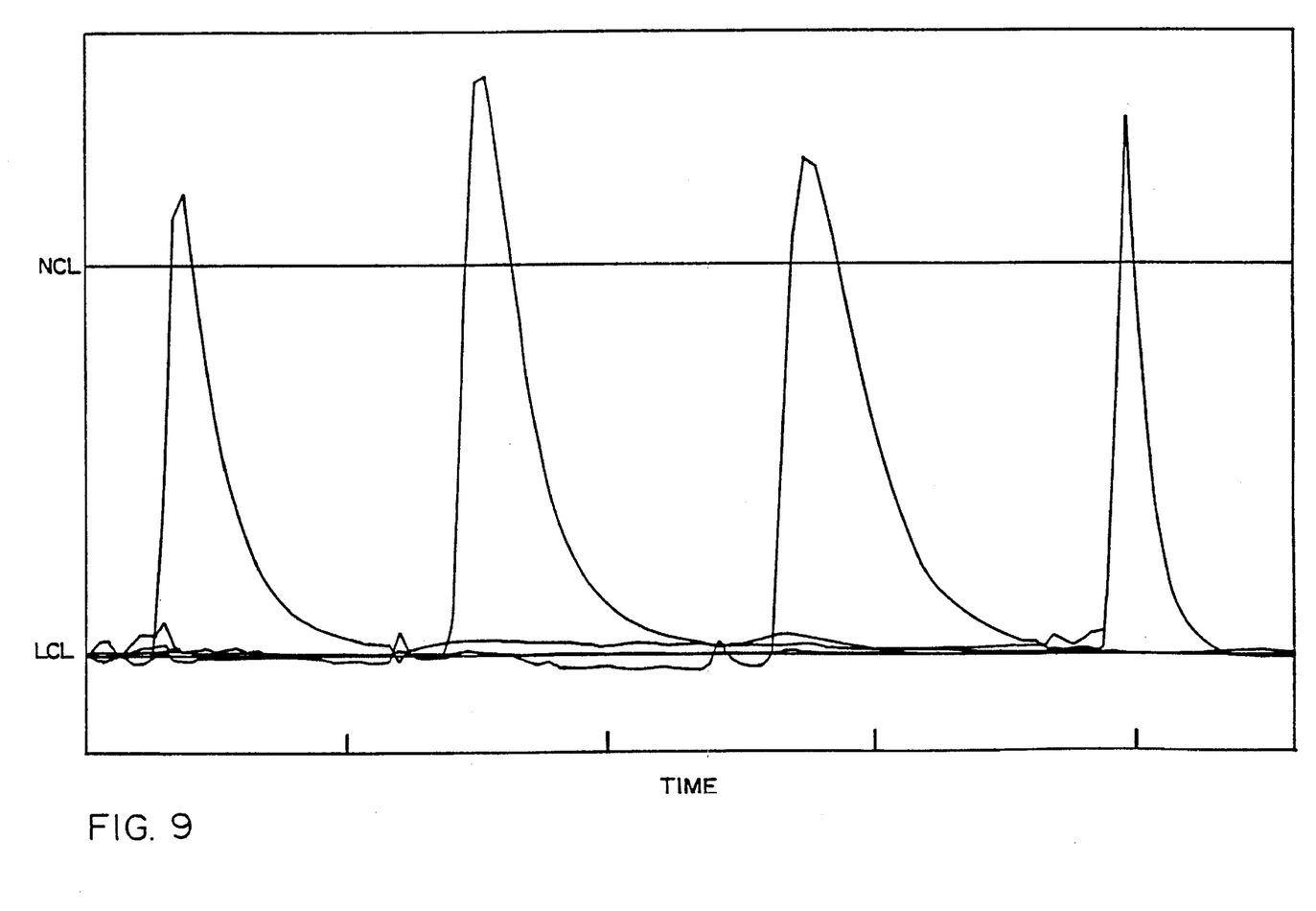
FIG. 9 shows exponential concentration curves derived by sparging the four specific substances involved in FIG. 8.

In order to envision the effect of a substance which does not have an exponential decay curve, consider FIGS. 8 and 9. Four substances are plotted in these figures: Benzene (B), Toluene (T), Xylene (X), and carbon dioxide (C). FIG. 8 is a spectral plot showing the simultaneous display of the spectra of these four substances; and Figure 9 is a concentration plot based on IR-sparging of these four substances.

In FIG. 8, the fingerprint region spectra of all four of the substances have been superimposed, in order to illustrate the degree to which they overlap. The identities of the curves are indicated by the first letter of the substance names (B, T, X and C). The rectangular outlines represent spectral regions that might be used to do a "P" matrix analysis.

In the absence of $CO_2$, the "P" matrix analysis works quite well. This is due to the fact that spectral regions can be selected where the absorbances have significantly different dependences on the concentrations of the three substances, i.e., for equal concentrations of the three substances, a single substance is the main contributor in each region.

If $CO_2$ is present, as is quite common, the analysis becomes much more difficult. $CO_2$ has a strong absorption band which completely overlaps the Benzene band. In principle, one should still be able to do a "P" matrix calculation by using a region of weak Benzene absorption (such as that marked "C") to quantify the $CO_2$. However, this does not work well for high concentrations, due to the fact that the IR absorbance of $CO_2$ is not linear in concentration.

FIG. 9 gives experimental concentration curves for each of the four substances sparged at a constant air flow rate. The half depletion times for each substance are indicated. As is apparent, $CO_2$ decays much more rapidly than the other three substances of interest. Thus, it should be possible to remove much of the $CO_2$ interference by using the method of this application. To do this, one would start by fitting the absorbance versus time data for each spectral point to a sum of functions representing the four chemical species. Three of these would most likely be simple exponentials. A first approximation for the dependence of $CO_2$ concentration on time could also be a simple exponential. However, since it is known that the absorbance of $CO_2$ is not linear in concentration, the simple exponential would not give good results at high concentrations.

Even though the $CO_2$ time dependence is not a simple exponential, it will still be a unique function, depending only on the initial concentration value and on time. The functionality can be experimentally determined, and then the measured data can be fitted to the result by varying the assumed initial concentration value. Even though the earlier part of this discussion assumed the use of exponential decay curves, they are not necessary. Any measurable and repeatable function of time and initial concentration can be used to fit the experimental data. This function does not have to be expressed as an equation but can simply be a table of calibration data. This fact can be quite valuable in the case of small molecules such as $CO_2$.

The foregoing lengthy explanation has demonstrated the analytical power obtainable by methods which combine spectral data information (e.g., FTIR data) with substance depletion rate information (such as that obtained from IR-sparging).

From the foregoing description, it will be apparent that the methods disclosed in this application will provide the significant functional benefits explained throughout the specification.

The following claims are intended not only to cover the specific methods disclosed, but also to cover the inventive concepts explained herein with the maximum breadth and comprehensiveness permitted by the prior art.

What is claimed is:

1. A method for measuring solutes in a solute-bearing liquid, which comprises:

passing a stream of gas bubbles through a fixed volume of the solute-bearing liquid, in order to include solute vapors in the stream;

analyzing the stream to establish the depletion rate curve of the solute or solutes in the liquid as a function of time;

comparing said depletion rate curve to one or more calibrated depletion rate curves representing known individual or combined solutes;

identifying all potential solutes which may be present in the liquid to be analyzed;

obtaining information concerning the vapor phase spectral characteristics of these potential solutes as well as their depletion rates when dissolved in a sample of liquid the same as or similar to the major component of the stream to be analyzed;

obtaining a set of samples having known liquid phase concentrations of the solutes of interest;

using a multivariate quantitation method in conjunction with data obtained with each of said samples and said spectral characteristics and depletion rates to develop a calibration valid for any combination of the identified potential solutes; and using said calibration in conjunction with said measured information regarding the concentrations of the solute vapors as a function of time to determine the concentrations of the individual solutes in the liquid.

2. A method for analysis of at least one of a plurality of solutes in a body of liquid, which comprises:

acquiring spectral-absorbance vs. wavelength data as a function of time over a spectral range within which the solutes exhibit absorption bands;

deriving from said spectral data depletion rate data unique to a separate wavelength channel; and using the depletion rate data in conjunction with the spectral-absorbance data to identify and measure solute concentration.

3. The method of claim 2 in which:

the spectral-absorbance vs. wavelength data is acquired by spectrographic analysis of gas whose constituency is determined by a sparging process.

4. The method of claim 3 in which the spectrographic analysis measures spectral absorbance across a span of infrared wavelengths.

5. The method of identifying a solute contained in a body of liquid, which comprises:

tentatively identifying said solute by analytical experimentation under given conditions;

determining the depletion rate curve of the unknown solute in the body of liquid by a depletion method comprising sparging a fixed, unreplenished volume of the solute-bearing liquid with a sparging gas stream of time-controlled flow volume, to include solute vapors in the stream;

analyzing the gas stream over time to establish the depletion rate curve of the solute or solutes from the liquid as a function of time under the same conditions;

establishing by calibration experimentation the depletion rate curve of the assumed solute in a body of liquid with said depletion method under the same conditions; and comparing the two depletion rate curves to check the tentative solute identification.

6. The method of claim 5 in which:

the depletion rate curves are obtained by an infrared sparging process in which (a) the solute is extracted from the liquid by a sparging process which transmits the solute as a gas to a gas cell; and (b) a spectroscopic analysis is performed on the gas in the cell at a plurality of time-spaced occasions in order to measure the depletion rate curve of the solute.

7. A method for measuring the concentrations of one or more solutes in a liquid, which comprises:

sparging a fixed, unreplenished volume of liquid with a flowing gas stream so as to transfer a portion of the solute to the gas stream;

controlling the flow rate of the gas stream;

analyzing solute vapor in the gas stream by means of an apparatus capable of obtaining data concerning the spectral absorbance of the gas stream;

repeating the analyzing step on samples taken from said gas stream at timed intervals in order to obtain time-dependent data concerning change of spectral absorbance; and deriving from the spectral characteristics and the time-dependence of the absorbance data depletion rate data for identifying one or more of the solutes in the liquid.

8. The method of claim 7, in which:

the analyzing apparatus is an infrared spectrometer including a gas cell sample chamber.

9. The method of claim 7 which also comprises:

determining from the time-dependent spectral data a unique exponential depletion curve for one or more of the solutes in the liquid.

10. The method of claim 7 which also includes:

performing a multivariate calibration including all solutes which might occur in the liquid stream to be analyzed; and treating the depletion rate of each solute as an independent parameter in setting up the calibration method.

11. The method of claim 10 which also includes:

treating a spectral channel which is common to two solutes as two independent channels if the solutes have clearly distinct depletion rates.

12. The method of claim 11 which also includes:

analyzing a mixture of solutes by first fitting the depletion rates for any spectral channels identified as being common to two or more of the calibration species to exponential functions having the known depletion rates for these species; and using the amplitude coefficients as independent data points for use in the multivariate calculation.

13. The method of claim 10 which also includes:

performing a multivariate calibration for each set of solutes having depletion rates falling within specific ranges.

14. The method of claim 13 which also includes:

analyzing an unknown mixture by first fitting the observed depletion rates for each spectral channel to a series of exponential functions;

grouping the exponential functions falling within said specific ranges into sets;

using the fitted amplitude coefficients for each of said sets to form a composite spectrum;

applying the chosen multiple component analysis method to each of said composite spectra so as to determine the concentration of each solute included in the calibration for the corresponding set.

15. A method for measuring the concentrations of one or more solutes in a liquid, which comprises:

passing a stream of gaseous bubbles through a fixed volume of liquid so as to transfer a portion of the solute to the gas stream;

controlling the flow rate of the gas stream;

analyzing solute vapor in the gas stream by means of an apparatus capable of obtaining data concerning the spectral absorbance of the gas stream;

repeating the analyzing step in order to obtain time-dependent data concerning change of spectral absorbance; and deriving from the spectral characteristics and the time-dependence of the absorbance data depletion rate data for identifying one or more of the solutes in the liquid;

determining from the time-dependent spectral data a unique exponential depletion curve for one or more of the solutes in the liquid;

determining the number of distinguishable solute depletion rates present by matching the time dependent information in each spectral channel to a sum of decreasing exponential functions;

determining the amplitude coefficients and depletion rates of the individual exponentials which best fit the data for each spectral region;

using the values of the amplitude coefficients obtained for each unique depletion rate as spectral absorbance values for multicomponent analysis; and performing a multicomponent analysis individually for each unique depletion rate or range of depletion rates, using a calibration in which the solutes represented have been selected to have depletion rates in the same ranges as said unique depletion rates.

16. A method for measuring solutes in a solute-bearing liquid, which comprises:

sparging a fixed, unreplenished volume of the solute-bearing liquid with a sparging gas stream of time-controlled flow volume, in order to include solute vapors in the stream;

analyzing the gas stream to establish the depletion rate curve of the solute or solutes from the liquid as a function of time; and comparing said depletion rate curve to at least one calibrated depletion rate curve representing known individual or combined solutes.

17. The method of claim 16 which includes:

measuring the infrared absorbance of the solutes in the stream.

18. The method of claim 17 in which:

infrared absorbance is measured by obtaining infrared spectra at timed intervals.

19. The method of claim 17 in which:

infrared absorbance is measured to obtain a depletion rate curve in one or more distinct spectral region(s).

20. The method of claim 19 in which:

infrared absorbance is measured by obtaining infrared spectra at timed intervals.

* * * * *